United States Patent [19]
Knoepfler

[11] Patent Number: 5,209,747
[45] Date of Patent: May 11, 1993

[54] ADJUSTABLE ANGLE MEDICAL FORCEPS

[76] Inventor: Dennis J. Knoepfler, 1383 Whitaker La., Amelia, Ohio 45101

[21] Appl. No.: 895,188

[22] Filed: Jun. 5, 1992

Related U.S. Application Data

[63] Continuation of Ser. No. 626,908, Dec. 13, 1990, abandoned.

[51] Int. Cl.⁵ ............................................. A61B 17/28
[52] U.S. Cl. ........................................ 606/16; 606/52;
606/205; 606/208; 604/22; 81/385
[58] Field of Search ................................. 606/205–208,
606/13, 16, 46, 51, 52; 128/751; 604/22;
81/177.8, 177.7, 177.75, 385, 386, 427.5

[56] References Cited
U.S. PATENT DOCUMENTS 724,046  3/1903  Sampson .
2,541,246 2/1951 Held .
3,709,215 1/1973 Richmond .
4,643,190 2/1987 Heimberger .
4,646,751 3/1987 Maslanka .
4,763,669 8/1988 Jaeger .
4,950,273 8/1990 Briggs .

OTHER PUBLICATIONS

Solos Endoscopy Catalog—1990.

Primary Examiner—Michael H. Thaler
Attorney, Agent, or Firm—Wood, Herron & Evans

[57] ABSTRACT

An adjustable angle medical forceps is disclosed which has a rotatable arm to which is attached a jaw element and which provides increased surgical dexterity for suturing with curved or straight needles, for dissecting bodily organs, and for isolating nerves, arteries, and the like. The forceps includes a laser fiber and irrigation and suction catheters for lasing, irrigating, and suctioning.

15 Claims, 4 Drawing Sheets

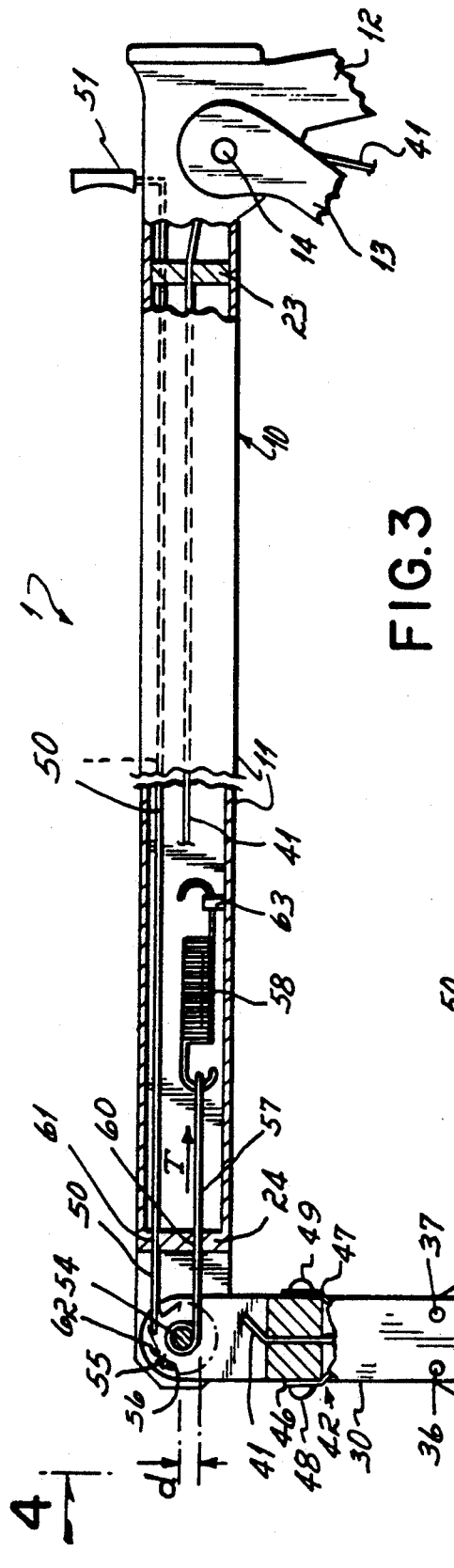
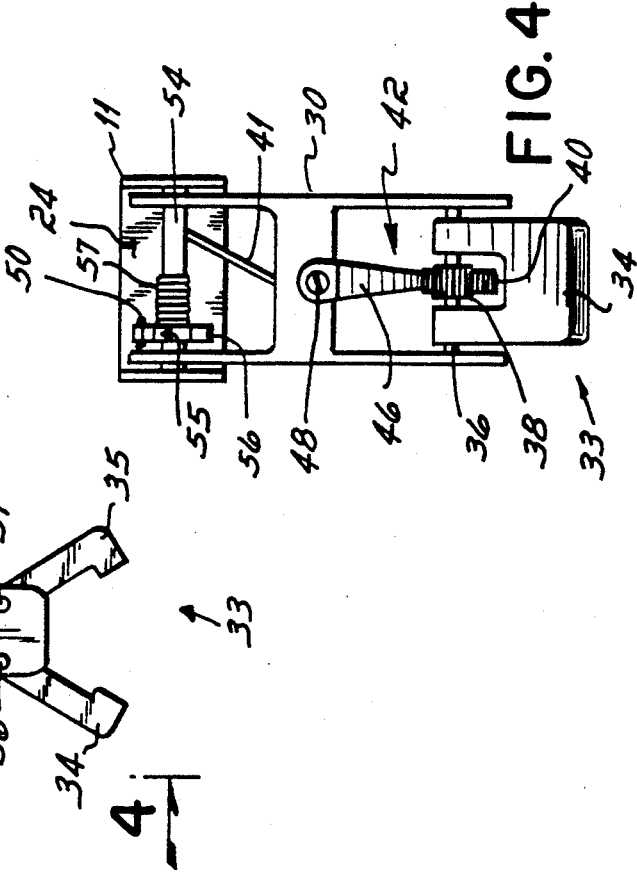
FIG.3
FIG.4

ADJUSTABLE ANGLE MEDICAL FORCEPS

This application is a continuation of application Ser. No. 626,908, filed Dec. 13, 1990 now abandoned.

BACKGROUND OF THE INVENTION

This invention relates generally to medical instruments, and more particularly to an adjustable angle medical forceps for use during a laparoscopy.

Several types of medical forceps have heretofore been utilized in various types of surgical procedures. For example, it has been found to be advantageous to use medical forceps wherein the jaw element was either movable with respect to the forcep's housing, or fixedly angled with respect to the forcep's housing. Such conventional instruments are disclosed, for example, in Maslanka U.S. Pat. No. 4,646,751, Jaeger U.S. Pat. No. 4,763,669, and Held U.S. Pat. No. 2,541,246.

However, in laparoscopic procedures, all of these conventional instruments are in varying degrees disadvantageous. In a laparoscopy, the forceps are inserted through a slender, cylindrical cannula, or sleeve, and into the patient's abdominal cavity. Hence, while the instrument of Maslanka '751, an improved flexible biopsy forceps, is useful for obtaining biopsies during gastroscopy and bronchoscopy, it is ill-suited for use during a laparoscopy because of its inherent instability. And, while the instrument of Held '246, a forceps having a rigid curved frame, is useful for endocholedochal sphincterotomy, it is ill-suited for use during a laparoscopy since this instrument cannot be inserted through a cannula.

On the other hand, the instrument of Jaeger '669 can be used during a laparoscopy since the cross-section of the jaw head oriented in a straight forward position can be made smaller than the crosssection of the main frame of the forceps and is therefore insertable through a cannula. Furthermore, since this surgical instrument has an adjustable jaw head which may be rotated relative to the main frame of the instrument during surgery, a limited degree of additional maneuverability and hence surgical dexterity is possible.

As can be seen, then, the flexible forceps and the fixedly angled forceps hereinabove described are not conducive for use during a laparoscopy. And, while a medical forceps with an adjustable angle jaw head is useful during a laparoscopy, this instrument nonetheless has several drawbacks. The relatively short distance from the jaws to the forcep's frame, when the jaws are oriented at a right angle with respect to the frame, allows for only minimal maneuverability during dissecting, suturing, and the like. Furthermore, the levers which actuate this rotatable jaw head of Jaeger '669 do not provide a sufficiently blunt instrument which is required for dissecting and isolating bodily organs, tissue, arteries, nerves, and the like.

SUMMARY OF THE INVENTION

It is one object of the present invention to provide a surgical instrument which can be used during a laparoscopy which provides additional distance between the jaw element and the forcep's frame when oriented at a right angle one with respect to another, and hence additional leverage, for suturing.

It is another object of the present invention to provide an adjustable angle medical forceps which can be inserted through a cannula for use during a laparoscopy.

It is a further object of the present invention to provide a medical forceps with which a surgeon can generate a larger arc while suturing, therefore facilitating suturing with either curved or straight needles.

Yet another object of the present invention is to provide a surgical instrument wherein the suturing of pyloroplasties and common bile ducts may be more easily performed.

Still another object of the present invention is to provide a medical instrument wherein dissecting near the base of the gall bladder is more easily facilitated.

Yet a further object of the present invention is to provide a medical instrument wherein the isolating of vagus nerves for future vagotomies is facilitated.

Still a further object of the present invention is to provide a medical instrument wherein the isolating of both the cystic duct and cystic artery may be facilitated.

The adjustable angle medical forceps of the present invention comprises first and second tubular housings, a movable jaw element, a handle, angle adjustment means to vary the angle of the jaw element and second tubular housing with respect to the first tubular housing, and jaw actuation means. To one end of the first tubular housing is attached a handle which is operable to open and close the jaw element via the jaw actuation means. The other end of the first tubular housing is pivotally connected to an end of the second tubular housing. The other end of the second tubular housing is connected to the jaw element. The angle adjustment means is operable to pivot the second tubular housing and the jaw element with respect to the first tubular housing.

The jaw element of the adjustable angle medical forceps of this invention comprises a pair of jaws each of which is pivotally supported on a shaft. The jaw shafts each have integral therewith a pinion gear.

The jaw actuation means of the adjustable angle medical forceps of this invention is predicated upon a flexible cable the ends of which are connected to opposing spring lever tensioning devices. One end of the flexible cable is connected to one such tensioning device which is mounted between the forceps handles. The other end of the flexible cable is connected to a rack gear cooperable with the pinion gears of the forcep's jaws, the rack gear being connected to another such tensioning device mounted in the second tubular housing. When the handles are squeezed together the handle spring levers are extended which pulls the flexible cable through the tubular housings thereby translating the rack gear with respect to the pinion gears of the jaws and closing the jaws. When the handles are released and spread apart the second tubular housing spring levers pull the flexible cable in the opposite direction which opens the jaws.

The angle adjustment means of the adjustable angle medical forceps of the present invention can be either of two mechanisms. A first mechanism contemplates a rotary shaft contained within the first tubular housing, with the rotary shaft having a rotary knob or dial on the forcep's handle end and a bevel gear on the other end. This bevel gear is cooperable with a second bevel gear which is fixedly attached within the second tubular housing. Therefore, when the rotary knob or dial is twisted the first bevel gear drives the second bevel gear and causes the second tubular housing and jaws therewith to pivot with respect to the first tubular housing.

The other angle adjustment device contemplates a push rod within the first tubular housing having an end grippable by a user at the forcep's handle end, and another end cooperable with a spring loaded ratchet mechanism such that when the push rod is pulled the ratchet device advances past the end of the push rod thereby causing the second tubular housing and hence jaws to pivot with respect to the first tubular housing. When the desired angle is achieved the push rod is pushed back into engagement with the ratchet thereby locking the ratchet and hence the second tubular housing and jaws therewith.

A laser fiber, an irrigation catheter, and a suction catheter may be threaded through either or both of the tubular housings, depending on the desired exit port location. The fiber and catheters could exit either at the distal end of the first tubular housing, or at the distal end of the second tubular housing. This would allow for simultaneous lasing, irrigating, and suctioning without the need to introduce a separate instrument.

The forceps handle may be outfitted with a unipolar port for attaching a cautery device, thereby allowing a user to maintain hemostasis during use of the instrument. This would likewise obviate the need for an additional cauterizing instrument.

One advantage of the present invention is that the manipulation of either curved or straight needles during suturing can be more easily accomplished.

Another advantage of the present invention is that suturing during a laparoscopy can be performed more efficiently since a greater suturing arc is provided by virtue of a greater moment arm between the jaw element and the main frame of a medical forceps.

Yet another advantage of the present invention is that the suturing of pyloroplasties, and common bile ducts, during a laparoscopy is more easily performed.

Yet a further advantage of the present invention is that the dissecting and isolating of body organs, tissue, arteries, nerves, and the like has been facilitated by providing a relatively blunt instrument for which the end may be angled at various orientations to, for example, dissect near the base of a gall bladder, or to, for example, isolate vagus nerves for future vagotomies.

Still a further advantage of the present invention is that tissue may be grasped with the forceps while simultaneously laser dissecting, irrigating, or suctioning.

These and other objects and advantages of the present invention will become more apparent to those having ordinary skill in the art to which the invention relates from the following description taken in conjunction with the accompanying drawings, in which:

BRIEF DESCRIPTION OF THE DRAWINGS

FIG. 3 is a view similar to FIG. 1 illustrating an alternative embodiment of the angle adjustment means.

FIG. 4 is a view taken along lines 4—4 of FIG. 3 further illustrating the alternative angle adjustment means.

DESCRIPTION OF PREFERRED EMBODIMENTS

Figure 1:
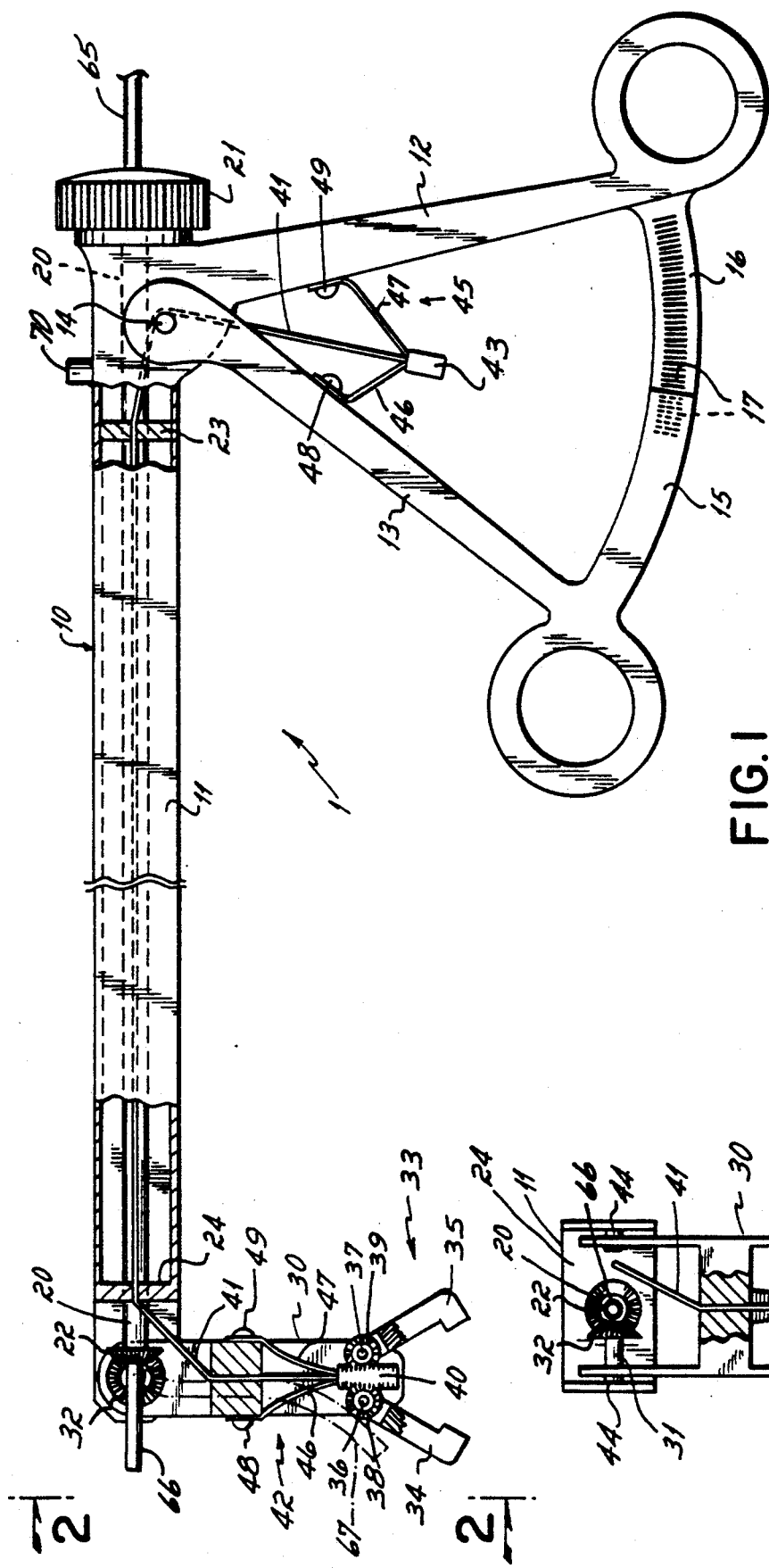
FIG. 1 is a partially broken away side view illustrating the invention which is the subject of this application.

Referring first to FIG. 1, an adjustable angle medical forceps 1 is shown. The forceps 1 is preferably fabricated from stainless steel and has a main frame 10 which comprises a first tubular housing 11 and integral therewith one-half of a scissors handle 12 fixedly attached to a first end of the first tubular housing 11. A complementing one-half scissors handle 13 is pivotally attached to the first end of the first tubular housing 11 by a pivot screw 14. The scissors handles 1 and 13 have cooperable latching arms 15 and 16 to maintain the scissors handles 12 and 13 at a desired location by virtue of their interacting latching teeth 17.

Contained within, and extending the length of the first tubular housing 11 is a hollow rotary shaft 20. This rotary shaft 20 has attached thereto a knob or dial 21 at the handle end of the rotary shaft 20. On the other end of the rotary shaft 20 is connected a bevel gear 22 which is likewise hollow. The first tubular housing 11 has an aft bulkhead 23 and a forward bulkhead 24. These bulkheads 23 and 24 contain holes (not shown) within which are press-fitted bushings (not shown). These bushing-outfitted bulkheads 23 and 24 rotatably support the rotary shaft 20 near its ends.

Figure 2:
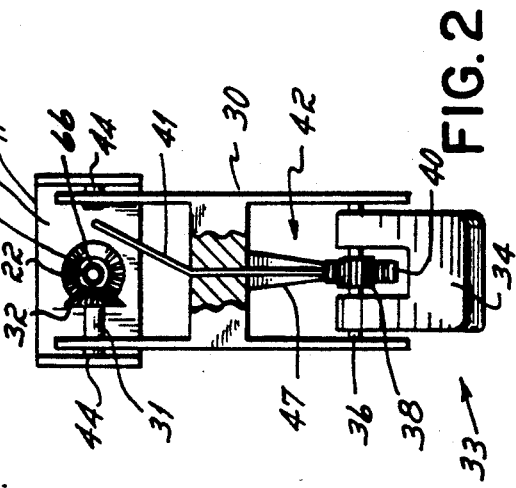
FIG. 2 is a view taken along lines 2—2 of FIG. 1 and illustrating the angle adjustment means and jaw actuation means.

Referring now to FIGS. 1 and 2, a first end of a second tubular housing 30 is pivotally connected to a second end of the first tubular housing 11 via pivots 44. A shaft 31 is an integral part of the second tubular housing 30 in that the second tubular housing 30 does not rotate with respect to the shaft 31. The shaft 31 and hence the second tubular housing 30 rotate with respect to the first tubular housing 11. A bevel gear 32 is press-fitted on, or otherwise fixedly attached to, the end of the shaft 31. A jaw pair 33 is connected to a second end of the second tubular housing 30. The jaw pair 33 is comprised of two separate jaw elements 34 and 35 which are fixedly attached to shafts 36 and 37, respectively. The ends of the shafts 36 and 37 reside within bushings (not shown) which are press-fitted into holes (not shown) in the sidewalls of the second tubular housing 30. Each shaft 36 and 37 has press fitted thereon pinion gears 38 and 39, respectively. These pinion gears are cooperable with a rack gear 40 which is connected to one end of a flexible cable 41. This flexible cable 41 extends the length of the tubular housings 11 and 30, the ends of which are connected to spring tensioning devices 42 and 45. Tension device 42 is mounted in housing 30 and tension device 45 is mounted between the scissors handles 12 and 13.

The spring tensioning device 45 comprises a pair of spring levers 46 and 47 which are attached to the insides of the scissors handles 12 and 13 via screws 48 and 49. The end of the flexible cable 41 is fixedly connected to the lower ends of both spring levers 46 and 47 by a slug 43. The spring tensioning device 42 likewise comprises a pair of spring levers 46 and 47 which are attached to the housing 30 via screws 48 and 49. The spring levers 46 and 47 are fixedly connected to the rack gear 40 and hence to the flexible cable 41.

The forceps 1 further includes a catheter 65 threaded through the shaft 20 and bevel gear 22, and hence the first tubular housing 11. This catheter 65 may contain a laser fiber and irrigation/suction catheters. The catheter 65 may exit at one of two locations: at the second end of the first tubular housing 66, or at the side of the second end of the second tubular housing 67 (shown in phantom). The forceps 1 also includes a unipolar port or bovie port 70 for connecting a cauterization device.

An alternative embodiment of the present invention is shown in FIGS. 3 and 4. In this embodiment, a push rod 50 is housed within the first tubular housing 11. This push rod 50 has an L-shaped end 51 which is easily grasped by a nurse or surgeon. The push rod 50 is supported near its ends within holes in the bulkheads 23 and 24 (one of which is shown at 61 in forward bulkhead 24), much like the rotary shaft 20. This push rod 50 is shown cooperating with a ratchet mechanism 55 which is used to advance the second tubular housing 30 rotationally about the end of the first tubular housing 11. This ratchet mechanism 55 is comprised of a ratchet 56 which is essentially a toothed sprocket and which is press-fitted on a shaft 54. This shaft 54 has wound thereon a flexible cable 57. This flexible cable 57 is wound counterclockwise about the shaft 54, with its first end being fixedly attached thereto, and its second end being attached to a forward end of a linear tension spring 58. This linear spring 58 has its aft end connected to a small boss 63 within the first tubular housing 11. The forward bulkhead 24 of the first tubular housing 11 has openings 60 and 61 for the flexible cable 57 and push rod 50, respectively. This bulkhead 24 with opening 61 therein serves as a base from which to cantilever the end of push rod 50, the end of which is cooperable with the teeth 62 of ratchet 56. In other words, the end of this push rod 50 resides between teeth 62 of the ratchet 56 and is sufficiently stiff such that when cantilevered off bulkhead 24 this rod 50 successfully resists potential counterclockwise rotation of ratchet 56 which would be in response to the torque generated by the product of the tension T in the flexible cable 57 created by the extension of the linear spring 58 and the distance d by which the flexible cable 57 is off-set from the shaft 54. This embodiment employs the same jaw actuation means as described earlier.

Figure 5:
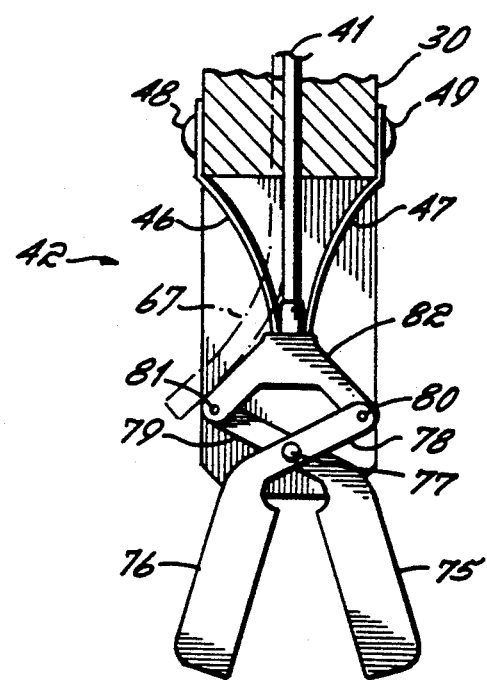
FIG. 5 is a side elevational view of an alternative embodiment of the jaw element.

An alternative embodiment of the jaw element of the present invention is shown in FIG. 5. The jaw element comprises a pair of jaws 75 and 76 hinged on a common shaft 77. The jaws further include reverse bent arms 78 and 79 which are pivotally connected by way of pivots 80 and 81 to an actuation tong 82. This tong 82 is connected to the end of the flexible cable 41. The jaw pair is spring loaded in an open condition by way of spring levers 46 and 47 attached to the second tubular housing 30 by way of screws 48 and 49.

Figure 6:
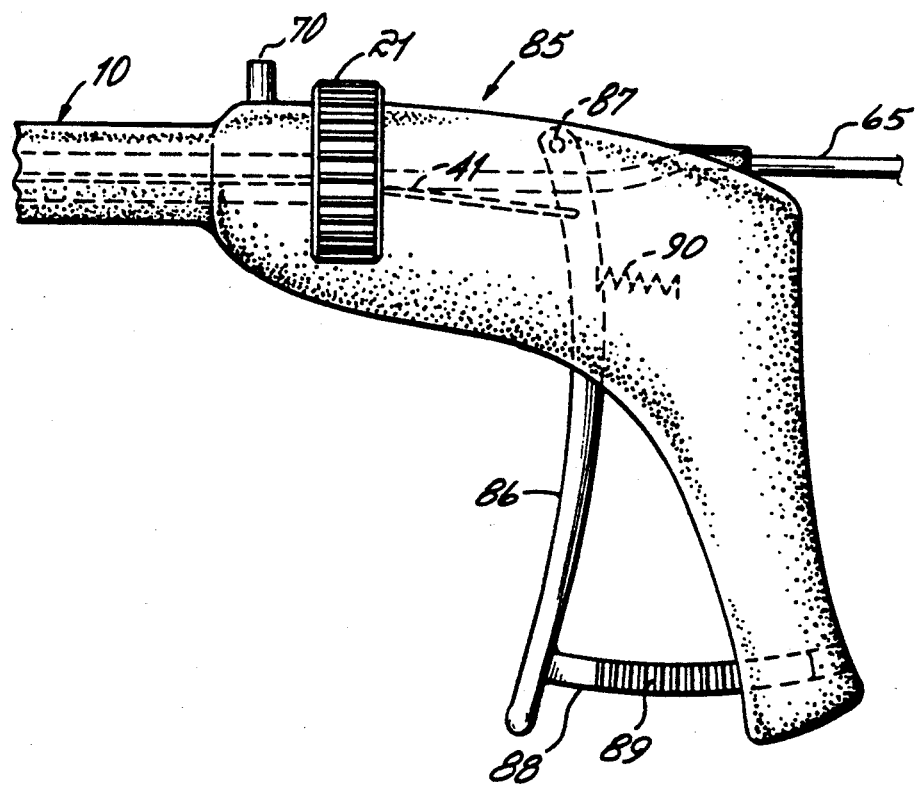
FIG. 6 is a side elevational view of an alternative embodiment of the forceps handle.
Figure 8:
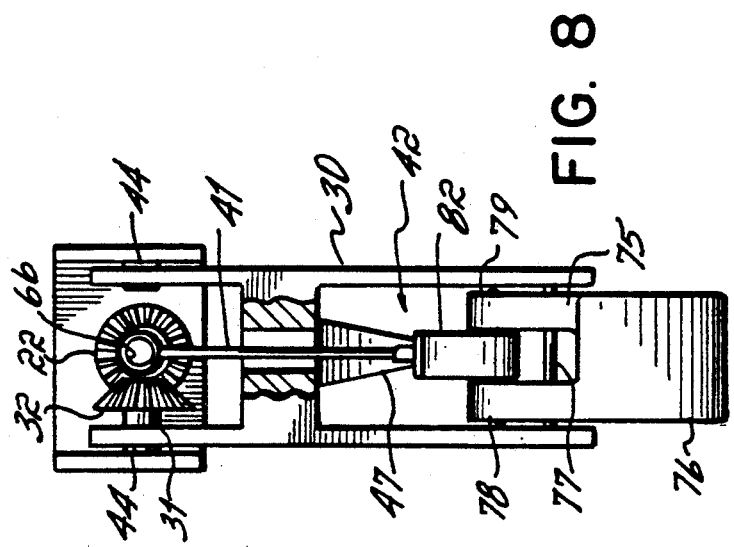
FIG. 8 is a view taken along lines 8—8 of FIG. 7 further illustrating the centralized flexible jaw actuation cable and laser/irrigation/suction catheter.
Figure 7:
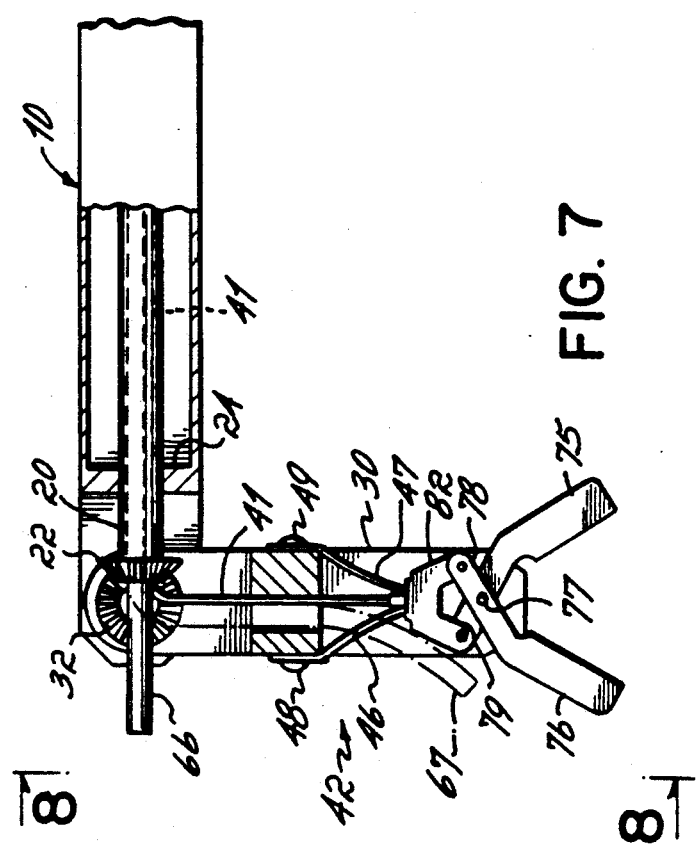
FIG. 7 is a partially broken away side view of the second tubular housing with alternative jaw element and a portion of the first tubular housing illustrating the centralized flexible jaw actuation cable and laser/irrigation/suction catheter.

An alternative embodiment of the forceps handle of the present invention is shown in FIG. 6. The forceps handle comprises a pistol grip style handle 85 and a complementing trigger style lever 86 hingably connected to the pistol grip handle 85 by way of a pin 87. The trigger lever 86 includes a latching arm 88 having latching teeth 89 thereon for cooperation with latching teeth (not shown) within the pistol grip handle 85. The flexible cable 41 is fixedly connected to this trigger lever 86, which is spring biased in an open condition by way of a compression spring 90 It will be appreciated that since the cable 41 connects to the lever 86 rearward of the knob 21, the cable 41 may desirably be passed through the shaft 20 and gear 22, thus centralizing both the catheter 65 and cable 41. FIGS. 7 and 8 illustrate this perhaps preferred arrangement.

Now describing the operation of the present invention, and referring first to the jaw element, the complementing scissors handle halves 12 and 13 are squeezed one towards the other. The lower ends of spring levers 46 and 47 of the tensioning device 45 are likewise pressed together, thereby causing each lever 46 and 47 to straighten out, the result being that the ends of these levers 46 and 47 to which is attached the flexible cable 41 are caused to move downwardly with respect to the scissors handles 12 and 13. At the same time the spring levers 46 and 47 of the tensioning device 42 are deflected upwards and away from the jaw pair 33. This results in the flexible cable 41 being pulled rearwardly with respect to the first and second housings 11 and 30. This translating cable 41 thereby causes the rack gear 40 to translate upwardly simultaneously causing each pinion gear 38 and 39 to rotate on shafts 36 and 37, respectively. This in turn causes the jaws 34 and 35 of the jaw pair 33 to rotate inwardly in a closing direction. The latching arms 15 and 16 of the scissors handles 12 and 13 are latched with teeth 17 at the desired location, thereby rendering the jaw pair 33 in the desired state. When the scissors handles 12 and 13 are released, the ends of the spring levers 46 and 47 of the tensioning device 45 move upwardly while the ends of the spring levers 46 and 47 of the tensioning device 42 move downwardly and toward the jaw pair 33 thereby pulling the flexible cable 41 forwardly and opening the jaw pair 33.

Describing now the rotation of the second housing 30 and jaw pair 33 with respect to the first housing 11, the knob 21 is first turned. This rotates the rotary shaft 20 which rotates the bevel gear 22. The bevel gear 22 engages the bevel gear 32 thereby driving same and the shaft 31 which is integral therewith. Since this shaft 31 is an integral part of the second tubular housing 30, this in turn causes the second tubular housing 30 to likewise rotate. Consequently, rotating the knob 21 clockwise causes the second tubular housing and hence the jaw pair 33 to rotate upwardly; rotating the knob 21 counterclockwise causes the second tubular housing 30 and jaw pair 33 to rotate downwardly.

Describing now the operation of the alternative embodiment of the present invention, the L-shaped end 51 of the push rod 50 is gripped by a user and pulled rearwardly. This causes the forward end of the push rod 50 to recede away from the ratchet teeth 62 of ratchet 56. The ratchet 56 is thereby freed and may now freely rotate counterclockwise under the torque generated by the product of the tension T in the flexible cable 57 created by the extension of the linear spring 58 and the distance d by which the flexible cable 57 is off-set from the shaft 31. The second tubular housing 30 and the jaw pair 33 are thereby pivoted downwardly. When the second housing 30 and jaw pair 33 reach the desired rotational orientation, the push rod 50 is pushed forwardly by the user until it engages the teeth 62 of the ratchet 56. The second tubular housing 30 and jaw pair 33 are then locked into position. To return the second tubular housing 30 and jaw pair 33 to their original position, the L-shaped end 51 of the push rod 50 is pulled rearwardly and the housing 30 is manually rotated clockwise to that original position.

During a laparoscopic surgical procedure, the second tubular housing 30 is rotated upwardly using either of the angle adjustment means (the knob 21 or the push rod 50) until that housing 30 is aligned with the first tubular housing 11 of the main frame 10. Next the scissors handles 12 and 13 are squeezed together causing the jaw pair 33 to close. When the jaw pair 33 is fully closed, and with the second tubular housing 30 colinear with the first tubular housing 11, the entire forceps 1 may then be inserted through a cannula into the patient's abdomen. Then the jaw pair 33 may be opened and closed, and the second tubular housing 30 and jaw pair 33 rotated with respect to the first tubular housing 11, as desired, for grasping, suturing, dissecting, and the like. Further, lasing, irrigating, suctioning, and cauterizing may be performed as desired.

To remove the forceps 1 from the patient's abdominal cavity the user need only reverse those steps taken to insert the forceps 1 through the cannula and into the abdominal cavity.

It will be appreciated that the alternative jaw arrangement (FIG. 5) and handle (FIG. 6) function much the same way as the scissors handle and geared jaw element of FIGS. 1 and 2, but may be desirable for either manipulative or manufacturing ease.

While I have described yet two embodiments of my invention, those skilled in the art will readily recognize adaptations and modifications which can be made and which will result in an improved medical instrument, without departing from the spirit or scope of the appended claims, by which I intend to be limited only.

What is claimed is:

1. An adjustable angle medical forceps adapted for a laparoscopic procedure comprising:
    a first tubular housing,
    a second tubular housing,
    a movable jaw pair,
    a handle,
    angle adjustment means, and
    jaw actuation means;
    said handle attached to a first end of said first tubular housing, said handle being operable to open and close said jaw pair via said jaw actuation mans, said first tubular housing having a second end to which is pivotally connected a first end of said second tubular housing, said angle adjustment means being operable to pivot said second tubular housing with respect to said first tubular housing, said second tubular housing having a second end to which is attached said jaw pair, the portion of said jaw actuation means and angle adjustment means near a distal end of said instrument being disposed substantially within said second tubular housing so that neither of said jaw actuation and angle adjustment means is exposed to surrounding tissue, said forceps thereby being adapted to bluntly dissect with said distal end thereof,
    whereby said forceps, initially configured generally straight, may be inserted through a cannula, placing said second tubular housing and moveable jaw pair within a patient's abdomen, and after insertion thereof said angle adjustment means may be manipulated externally of the cannula and the patient's abdomen, to articulate said second tubular housing and jaw pair into a desired angular configuration within the patient's abdomen, said jaw actuation means then being operable to actuate said jaw pair for grasping, suturing and dissecting, said second tubular housing spacing said jaw pair from said first tubular housing and providing, when angled with respect to said first tubular housing, increased leverage, maneuverability and dexterity for suturing, dissecting and the like.

2. The adjustable angle medical forceps of claim 1 wherein said movable jaw pair includes a pair of jaw elements, each jaw element of said pair being pivotally supported on a shaft and having integral therewith a pinion gear pivotally supported on said shaft.

3. The adjustable angle medical forceps of claim 2 wherein said jaw actuation means includes a flexible cable having a first end connected to said handle via spring tensioning means, said flexible cable extending through said first and second tubular housings and having a second end to which is attached a rack gear cooperable with said pinion gears of said jaw elements, wherein when said handle is squeezed said spring tensioning means retracts said flexible cable into said first and second tubular housings thereby translating said rack gear with respect to said pinion gears and closing said pair.

4. The adjustable angle medical forceps of claim 1 further including:
    laser means,
    irrigation means,
    suction means, and
    cauterization means.

5. The adjustable angle medical forceps of claim 4 wherein said laser means comprises a laser fiber threaded through said first tubular housing, and said irrigation and suction means comprises irrigation and suction catheters threaded through said first tubular housing, each said laser fiber, irrigation catheter, and suction catheter having an exit port near said second end of said first tubular housing.

6. The adjustable angle medical forceps of claim 4 wherein said laser means comprises a laser fiber threaded through said first and second tubular housings, and said irrigation and suction means comprises irrigation and suction catheters threaded through said first and second tubular housings, each said laser fiber, irrigation catheter, and suction catheter having an exit port at a side of said second tubular housing near said second end.

7. The adjustable angle medical forceps of claim 1 wherein said movable jaw pair includes a pair of jaw elements, said pair of jaw elements being pivotally supported on a common shaft, said jaw elements having integral therewith a scissors mechanism means.

8. The adjustable angle medical forceps of claim 7 wherein said jaw actuation means includes a flexible cable having a first end connected to said handle via spring tensioning means, said flexible cable extending through said first and second tubular housings and having a second end attached to said scissors mechanism means, wherein when said handle is squeezed said spring tensioning means retracts said flexible cable into said first and second tubular housings, thereby actuating said scissors mechanism means and closing said jaw pair.

9. The adjustable angle medical forceps of claim 1 wherein said angle adjustment means extends through said first tubular housing.

10. An adjustable angle medical forceps comprising:
    a first tubular housing;
    a second tubular housing,
    a movable jaw element, a handle,
angle adjustment means, and
jaw actuation means;
said handle attached to a first end of said first tubular housing, said handle operable to open and close said jaw element via said jaw actuation means, said first tubular housing having a second end to which is pivotally connected a first end of said second tubular housing, said angle adjustment means operable so as to pivot said second tubular housing with respect to said first tubular housing, said second tubular housing having a second end to which is attached said jaw element;
said movable jaw element including a pair of jaws, each jaw of said pair being pivotally supported on a shaft and having integral therewith a pinion gear pivotally supported on said shaft;
said jaw actuation means including a flexible cable having a first end connected to said handle via spring tensioning means, said flexible cable extending through said first and second tubular housings and having a second end to which is attached a rack gear cooperable with said pinion gears of said jaws, wherein when said handle is squeezed said spring tensioning means retracts said flexible cable into said first and second tubular housings thereby translating said rack gear with respect to said pinion gears and closing said jaws;
said angle adjustment means including a rotary shaft contained within said first tubular housing, said rotary shaft having a first end to which is attached a rotary knob and a second end to which is attached a first bevel gear, said first bevel gear cooperable with a second bevel gear, said second bevel gear having an axle of rotation oriented at a right angle with respect to an axis of rotation of said first bevel gear and being fixedly attached within and to said first end of said second tubular housing, said axis of rotation of said second bevel gear being at a right angle to a centerline axis of said second tubular housing, wherein when said rotary knob is twisted said first bevel gear drives said second bevel gear causing said second tubular housing to pivot with respect to said first tubular housing.

11. An adjustable angle medical forceps comprising:
a first tubular housing,
a second tubular housing,
a movable jaw element,
a handle,
angle adjustment means, and
jaw actuation means;
said handle attached to a first end of said first tubular housing, said handle operable to open and close said jaw element via said jaw actuation means, said first tubular housing having a second end to which is pivotally connected a first end of said second tubular housing, said angle adjustment means operable so as to pivot said second tubular housing with respect to said first tubular housing, said second tubular housing having a second end to which is attached said jaw element;
said movable jaw element including a pair of jaws, each jaw of said pair being pivotally supported on a shaft and having integral therewith a pinion gear pivotally supported on said shaft;
said jaw actuation means including a flexible cable having a first end connected to said handle via spring tensioning means, said flexible cable extending through said first and second tubular housings and having a second end to which is attached a rack gear cooperable with said pinion gears of said jaws, wherein when said handle is squeezed said spring tensioning means retracts said flexible cable into said first and second tubular housings thereby translating said rack gear with respect to said pinion gears and closing said jaws;
said angle adjustment means including a push rod contained within said first tubular housing, said push rod having a first end with gripping means grippable by a user and a second end operable as a latch and cooperable with a spring loaded ratchet, said ratchet being fixedly attached within and to said first end of said second tubular housing, wherein when said first end of said push rod is pulled said ratchet advances past said latch causing said second tubular housing to pivot with respect to said first tubular housing.

12. An adjustable angle medical forceps comprising:
a first tubular housing,
a second tubular housing,
a movable jaw element,
a handle,
angle adjustment means, and
jaw actuation means;
said handle attached to a first end of said first tubular housing, said handle operable to open and close said jaw element via said jaw actuation means, said first tubular housing having a second end to which is pivotally connected a first end of said second tubular housing, said angle adjustment means operable so as to pivot said second tubular housing with respect to said first tubular housing, said second tubular housing having a second end to which is attached said jaw element;
said movable jaw element including a pair of jaws, said pair of jaws being pivotally supported on a common shaft, said jaws having integral therewith a scissors mechanism means;
said jaw actuation means including a flexible cable having a first end connected to said handle via spring tensioning means, said flexible cable extending through said first and second tubular housings and having a second end attached to said scissors mechanism means, wherein when said handle is squeezed said spring tensioning means retracts said flexible cable into said first and second tubular housings, thereby actuating said scissors mechanism means and closing said jaws;
said angle adjustment means including a rotary shaft contained within said first tubular housing, said rotary shaft having a first end to which is attached a rotary knob and a second end to which is attached a first bevel gear, said first bevel gear cooperable with a second bevel gear, said second bevel gear having an axis of rotation oriented at a right angle with respect to an axis of rotation of said first bevel gear and being fixedly attached within and to said first end of said second tubular housing, said axis of rotation of said second bevel gear being at a right angle to a centerline axis of said second tubular housing, wherein when said rotary knob is twisted said first bevel gear drives said second bevel gear causing said second tubular housing to pivot with respect to said first tubular housing.

13. An adjustable angle medical forceps comprising:
a first tubular housing, a second tubular housing,
a movable jaw element,
a handle,
angle adjustment means, and
jaw actuation means;
said handle attached to a first end of said first tubular housing, said handle operable to open and close said jaw element via said jaw actuation means, said first tubular housing having a second end to which is pivotally connected a first end of said second tubular housing, said angle adjustment means operable so as to pivot said second tubular housing with respect to said first tubular housing, said second tubular housing having a second end to which is attached said jaw element;
said movable jaw element including a pair of jaws, said pair of jaws being pivotally supported on a common shaft, said jaws having integral therewith a scissors mechanism means;
said jaw actuation means including a flexible cable having a first end connected to said handle via spring tensioning means, said flexible cable extending through said first and second tubular housings and having a second end attached to said scissors mechanism means, wherein when said handle is squeezed said spring tensioning means retracts said flexible cable into said first and second tubular housings, thereby actuating said scissors mechanism means and closing said jaws;
said angle adjustment means including a push rod contained within said first tubular housing, said push rod having a first end with gripping means grippable by a user and a second end operable as a latch and cooperable with a spring loaded ratchet, said ratchet being fixedly attached within and to said first end of said second tubular housing, wherein when said first end of said push rod is pulled said ratchet advances past said latch causing said second tubular housing to pivot with respect to said first tubular housing.

14. An adjustable angle scopic device comprising:
a first tubular housing,
a second tubular housing,
a movable jaw pair,
a handle,
angle adjustment means, and
jaw actuation means;
said handle attached to a first end of said first tubular housing, said handle being operable to open and close said jaw pair via said jaw actuation means, said first tubular housing having a second end to which is pivotally connected a first end of said second tubular housing, said angle adjustment means being operable to pivot said second tubular housing with respect to said first tubular housing, said second tubular housing having a second end to which is attached said jaw pair, the portion of said jaw actuation means and angle adjustment means near a distal end of said instrument being disposed substantially within said second tubular housing so that neither of said jaw actuation and angle adjustment means is exposed to surrounding tissue, said forceps thereby being adapted to bluntly dissect with said distal end thereof,
whereby said forceps, initially configured generally straight, may be inserted through a cannula, placing said second tubular housing and moveable jaw pair within a patient's abdomen, and after insertion thereof said angle adjustment means may be manipulated externally of the cannula and the patient's abdomen, to articulate said second tubular housing and jaw pair into a desired angular configuration within the patient's abdomen, said jaw actuation means then being operable to actuate said jaw pair for grasping, suturing and dissecting, said second tubular housing spacing said jaw pair from said first tubular housing and providing, when angled with respect to said first tubular housing, increased leverage, maneuverability and dexterity for suturing, dissecting and the like.

15. An adjustable angle medical forceps adapted for a laparoscopic procedure comprising:
a first slender, elongated member,
a second slender, elongated member,
a movable jaw pair,
a handle,
angle adjustment means, and
jaw actuation means;
said handle attached to a first end of said first member, said handle being operable to open and close said jaw pair via said jaw actuation means, said first member having a second end with means for pivoting relative thereto said second member, said angle adjustment means being operable to pivot said second member with respect to said first member, said second member having a distal end to which is attached said jaw pair, the portion of said jaw actuation means near a distal end of said instrument being disposed substantially within said second member, said forceps thereby being adapted to bluntly dissect with said distal end thereof,
whereby said forceps, initially configured generally straight, may be inserted through a cannula, placing said second member and moveable jaw pair within a patient's abdomen, and after insertion thereof said angle adjustment means may be manipulated to articulate said second member and jaw pair into a desired angular configuration within the patient's abdomen, said jaw actuation means then being operable to actuate said jaw pair for grasping, suturing and dissecting, said second member spacing said jaw pair from said first member and providing, when angled with respect to said first member, increased leverage, maneuverability and dexterity for suturing, dissecting and the like.

* * * * *